US009687181B2

(12) United States Patent
Leobandung et al.

(10) Patent No.: US 9,687,181 B2
(45) Date of Patent: Jun. 27, 2017

(54) SEMICONDUCTOR DEVICE TO BE EMBEDDED WITHIN A CONTACT LENS

(71) Applicant: International Business Machines Corporation, Armonk, NY (US)

(72) Inventors: Effendi Leobandung, Stormville, NY (US); Ghavam G. Shahidi, Pound Ridge, NY (US)

(73) Assignee: International Business Machines Corporation, Armonk, NY (US)

( * ) Notice: Subject to any disclaimer, the term of this patent is extended or adjusted under 35 U.S.C. 154(b) by 325 days.

(21) Appl. No.: 14/488,435

(22) Filed: Sep. 17, 2014

(65) Prior Publication Data

US 2016/0073872 A1    Mar. 17, 2016

(51) Int. Cl.
 *A61B 5/00* (2006.01)
 *A61B 5/145* (2006.01)

(52) U.S. Cl.
CPC ...... *A61B 5/14546* (2013.01); *A61B 5/14532* (2013.01); *A61B 5/6821* (2013.01); *A61B 5/7225* (2013.01); *A61B 2560/0214* (2013.01); *A61B 2562/12* (2013.01)

(58) Field of Classification Search
CPC . A61B 5/14532; A61B 5/6821; A61B 5/0002; A61B 5/0015; A61B 5/145; A61B 2560/00; A61B 2560/0204; A61B 2560/0214; A61B 2562/16; A61B 2562/164
See application file for complete search history.

(56) References Cited

U.S. PATENT DOCUMENTS

| 5,528,222 | A  | 6/1996  | Moskowitz et al. |
| 8,534,831 | B2 | 9/2013  | Tepedino, Jr. et al. |
| 8,608,310 | B2 | 12/2013 | Otis et al. |
| 8,632,182 | B2 | 1/2014  | Chen et al. |
| 2006/0183986 | A1 | 8/2006 | Rice et al. |
| 2010/0004523 | A1 | 1/2010 | August et al. |

(Continued)

OTHER PUBLICATIONS

S.-S. Hsu et al., "A 60-GHz millimeter-wave CPW-fed Yagi antenna fabricated by using 0.18um-CMOS technology," IEEE Electron Device Letters, vol. 29, No. 6, Jun. 2008, pp. 625-627.

(Continued)

*Primary Examiner* — Eric Winakur
(74) *Attorney, Agent, or Firm* — L. Jeffrey Kelly; Douglas M. Crockatt

(57) ABSTRACT

A semiconductor device embedded within a contact lens is provided. The semiconductor device may include a sensor that determines one or more properties associated with an analyte within fluid surrounding the contact lens, and a processing circuit that is coupled to the sensor. The processing circuit generates a signal associated with the one or more determined properties associated with the analyte. A power supply is coupled to the processing circuit for providing DC power to the processing circuit. A boost circuit coupled to the power supply may then increase the provided DC power of the power supply for transmitting the signal generated by the processing circuit. An antenna is coupled to the processing circuit for transmitting the generated signal, whereby the sensor, the processing circuit, the power supply, the boost circuit, and the antenna are contained on a single unpackaged semiconductor die.

19 Claims, 10 Drawing Sheets

(56) References Cited

U.S. PATENT DOCUMENTS

2013/0194540 A1* 8/2013 Pugh ..................... A61F 2/1635
351/159.03
2014/0191253 A1* 7/2014 Haslbeck ............ H01L 31/0203
257/82
2014/0194708 A1* 7/2014 Ho .................... A61B 5/14552
600/318

OTHER PUBLICATIONS

B. A. Parviz, "Augmented reality in a contact lens," IEEE Spectrum, Sep. 2009, downloaded from the Internet May 15, 2014, spectrum.ieee.org/biomedical/bionics/augmented-reality-in-a-contact-lens/0 and spectrum.ieee.org/biomedical/bionics/augmented-reality-in-a-contact-lens/0/eyesb1.

W. D. Jones, "A Form-fitting Photovoltaic Artificial Retina," IEEE Spectrum, Dec. 2009, downloaded from the Internet May 15, 2014, spectrum.ieee.org/biomedical/bionics/a-formfitting-photovoltaic-artificial-retina.

Y.-T. Liao et al., "A 3-uW CMOS glucose sensor for wireless contact-lens tear glucose monitoring," IEEE Journal of Solid-State Circuits, vol. 47, No. 1, Jan. 2012, pp. 335-344.

A. R. Lingley et al., "A contact lens with integrated micro solar cells," Microsystem Technologies, vol. 18, No. 4, 2012, pp. 453-458.

Treehugger. "Solar Powered Eyes-Powering Electronic Contact Lenses and Retina with Sunlight", Accessed on Jul. 16, 2014, pp. 1-3, http://www.treehugger.com/clean-technology/solar-powered-eyes-power/.

* cited by examiner

Cross Section View

Plan View

410 →

Cross Section View

410 →

Plan View

SEMICONDUCTOR DEVICE TO BE EMBEDDED WITHIN A CONTACT LENS

BACKGROUND

The present invention generally relates to semiconductor devices, and more particularly, to semiconductor devices embedded within contact lenses.

Contact lenses are widely used by the general population to correct and enhance visual perception. In addition, embedded electronic devices have been incorporated within contact lenses to monitor body chemistry. For example, through the use of sensors and integrated circuits embedded within a contact lens, glucose levels in the tears of a diabetic contact lens wearer may be determined.

Referring to FIG. 1, a cross-sectional diagram of a device 100A to be embedded within a contact lens, as known in the art, is illustrated. Device 100A contains one or more discrete components 101. The one or more discrete components 101 include a semiconductor device 102A having a sensor 104A, a radio-frequency identification (RFID) antenna 106A, and a processing circuit 108A. The one or more discrete components 101 are enclosed in individual packages and may, therefore, be electrically coupled together via a substrate 112 (i.e., a circuit board) using one or more solder connections 110. Solder connections 110 may be formed using a multitude of methods, such as the controlled collapse chip connection (C4) method. The mounting of discrete components 101 to substrate 112 may result in device 100A having a large size that requires device 100A to be embedded within a thicker contact lens. This in turn can lead to a decrease in wearer comfort. The large size of device 100A may also render device 100A visually perceptible to a contact lens wearer, such that the device 100A may at least partially obstruct the contact lens wearer's field of vision.

Furthermore, device 100A utilizes RFID and is therefore powered by the presence of a radio-frequency (RF) field being received by antenna 106A. The wearer of the contact lens is, therefore, subjected to in-bound RF radiation in order to retrieve data collected by device 100A through sensor 104A. This RF radiation may impair the contact lens wearer's health (e.g., burns to the eye, brain tumor).

BRIEF SUMMARY

According to one embodiment, an integrated semiconductor device may be embedded within a contact lens, whereby the embedded integrated semiconductor chip device is formed on a single unpackaged die for, among other things, transmitting data associated with analytes that exist within tears surrounding the contact lens of a contact lens wearer.

According to one exemplary embodiment, a semiconductor device that may be embedded within a contact lens is provided. The semiconductor device may include, among other things, a sensor that determines one or more properties associated with an analyte within fluid surrounding the contact lens. A processing circuit may be coupled to the sensor, whereby the processing circuit generates a signal associated with the one or more determined properties associated with the analyte. A power supply may be coupled to the processing circuit to provide direct current (DC) power to the processing circuit. A boost circuit may be coupled to the power supply, whereby the boost circuit increases the provided DC power to the processing circuit. An antenna may be coupled to the processing circuit for transmitting the generated signal. The sensor, the processing circuit, the power supply, the boost circuit, and the antenna may be contained on a single unpackaged semiconductor die.

According to another exemplary embodiment, a method for processing one or more properties associated with an analyte within fluid surrounding a contact lens is provided. The method may include sensing the one or more properties associated with the analyte within fluid surrounding the contact lens using a sensor embedded within the contact lens. A radio frequency signal may be generated using a processing circuit embedded within the contact lens, based on the sensing of the one or more properties associated with the analyte within fluid surrounding the contact lens. DC power may be generated by a power supply embedded within the contact lens, and the generated power may be increased over a time interval using a capacitor boost circuit embedded within the contact lens. Using the increased generated power, the generated radio frequency signal may be transmitted in an outward direction relative to an outer surface of the contact lens, whereby the generated radio frequency signal includes data associated with the sensing of the one or more properties associated with the analyte. The embedded sensor, the embedded processing circuit, the embedded power supply, and the embedded capacitor boost circuit may be contained on a single unpackaged semiconductor die embedded within the contact lens.

According to another exemplary embodiment, a design structure tangibly embodied in a machine readable medium for designing, manufacturing, or testing an integrated circuit is provided. The design structure may include, among other things, a sensor that determines one or more properties associated with an analyte within fluid surrounding a contact lens. A processing circuit may be coupled to the sensor, whereby the processing circuit generates a signal associated with the one or more determined properties associated with the analyte. A power supply may be coupled to the processing circuit to provide DC power to the processing circuit. A boost circuit may be coupled to the power supply, whereby the boost circuit increases the provided DC power to the processing circuit. An antenna may be coupled to the processing circuit for transmitting the generated signal. The sensor, the processing circuit, the power supply, the boost circuit, and the antenna may be contained on a single unpackaged semiconductor die embedded within the contact lens.

BRIEF DESCRIPTION OF THE SEVERAL VIEWS OF THE DRAWINGS

The drawings are not necessarily to scale. The drawings are merely schematic representations, not intended to portray specific parameters of the invention. The drawings are intended to depict only typical embodiments of the invention. In the drawings, like numbering represents like elements.

DETAILED DESCRIPTION

The following exemplary embodiments describe an integrated semiconductor device that may be embedded within a contact lens, whereby the embedded integrated semiconductor chip device is formed on a single unpackaged die for, among other things, transmitting data associated with analytes that exist within tears surrounding the contact lens of a contact lens wearer. The embedded integrated semiconductor chip device formed on the single unpackaged die may include a completely self-contained semiconductor chip with no requisite need for interfacing with one or more other components through I/O pins such as wirebonds and/or C4 connections.

Figure 2A:
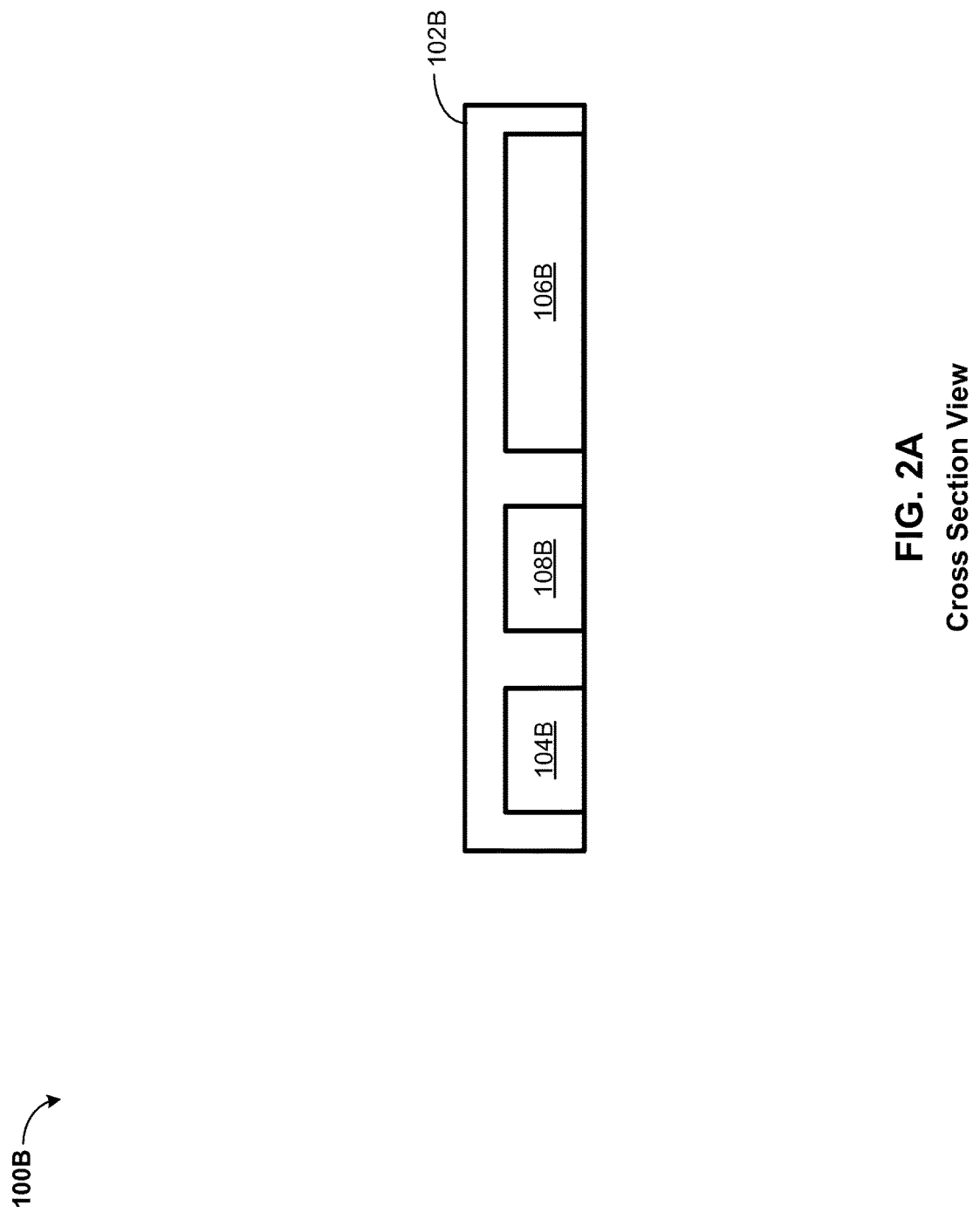
FIGS. 2A-2B are respective cross-section and plan views of a semiconductor device to be embedded within a contact lens, according to one exemplary embodiment.
Figure 2B:
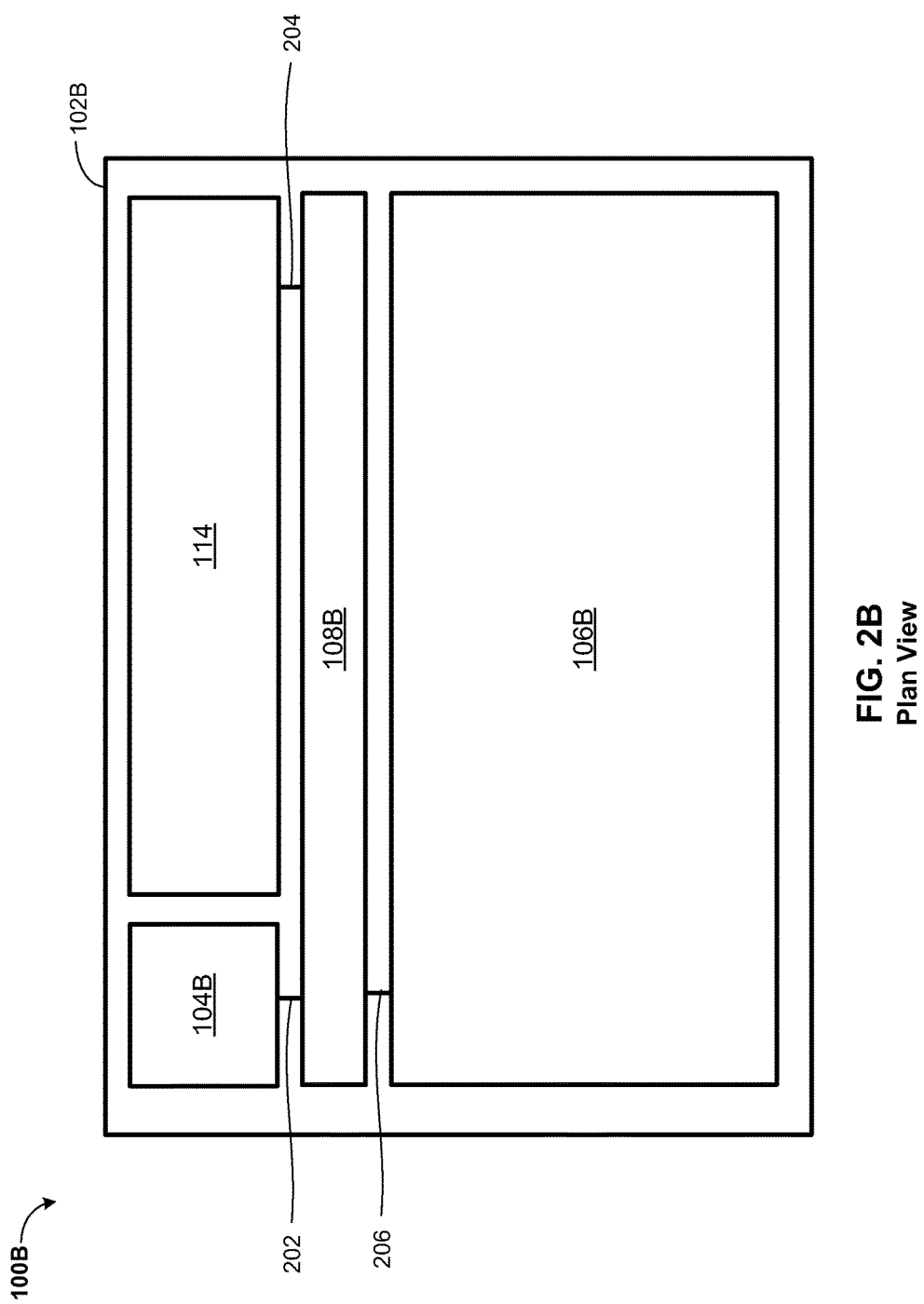

Referring to FIGS. 2A and 2B, respective cross-section and plan views of a semiconductor device 100B to be embedded within a contact lens according to one exemplary embodiment are depicted. Semiconductor device 100B may include, among other things, a sensor 104B, an antenna 106B, a processing circuit 108B, and a power supply 114. Sensor 104B, antenna 106B, processing circuit 108B, and power supply 114 may be formed on a substrate 102B (i.e., a diced wafer) and may, accordingly, be utilized within semiconductor device 100B without individual packages. Sensor 104B, power supply 114, and antenna 106B may each be connected to processing circuit 108B by data link 202, power link 204, and data link 206, respectively.

Figure 1:
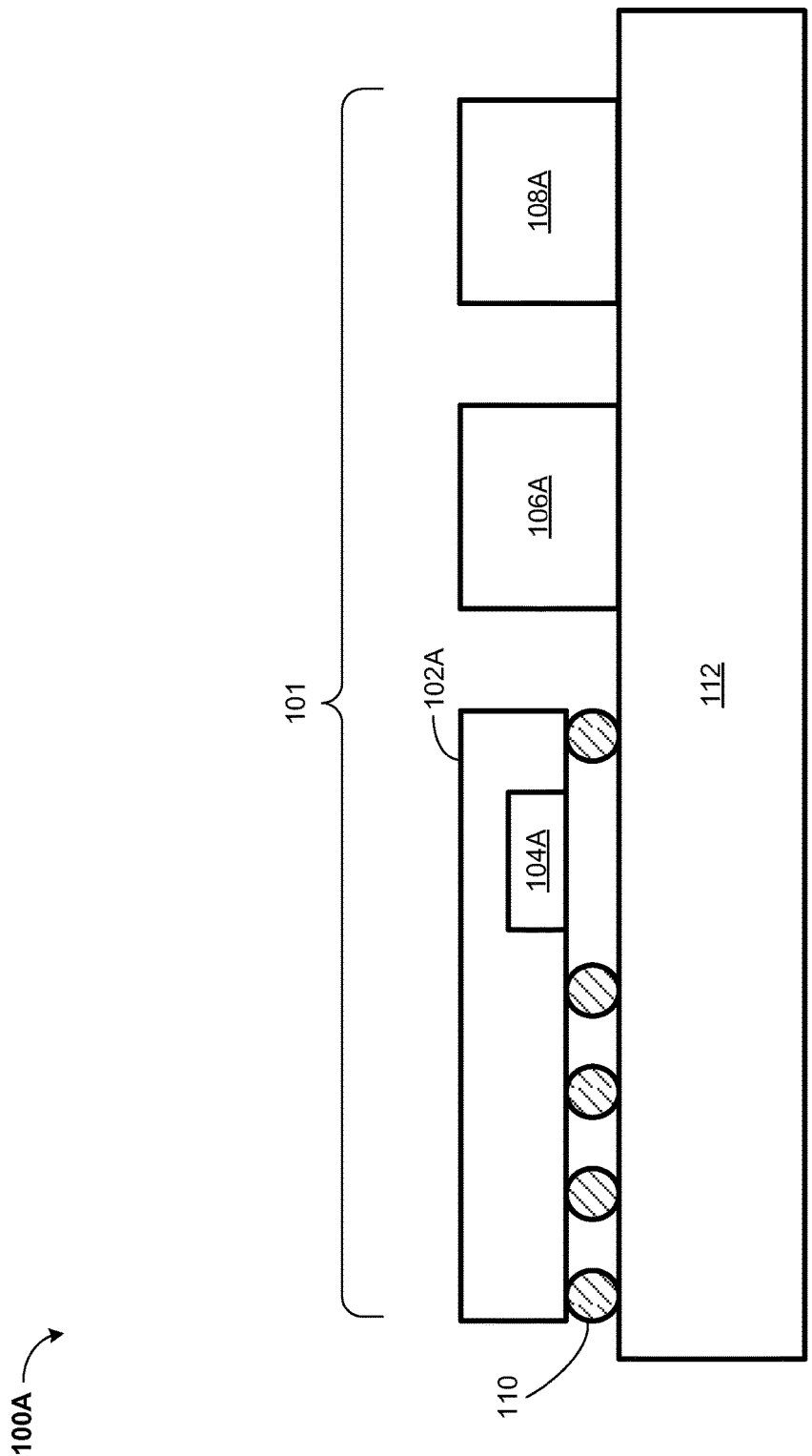
FIG. 1 is a cross-sectional diagram of a device to be embedded within a contact lens, as conventionally known.

In operation, tears of a wearer of a contact lens containing semiconductor device 100B may contain one or more analytes, such as glucose, various medications, or ionic compounds (e.g., salts of calcium, potassium, sodium, etc.). Sensor 104B may detect a property corresponding to the analyte, such as the presence or absence of the analyte or a concentration value associated with the analyte. Upon detecting the property corresponding to the analyte, sensor 104B may transmit data corresponding to the detection of the property along data link 202. Processing circuit 108B may receive the property data from sensor 104B via data link 202 and package it in a form to be transmitted to a reader external to the contact lens (not depicted). Processing circuit 108B may transmit the packaged data over data link 206 and antenna 106B. Antenna 106B may be, among other things, a Yagi antenna operating within at least of portion of the millimeter-wave band. Accordingly, antenna 106B may be of a smaller size than antenna 106A (FIG. 1A) as conventionally known in the art. The portion of the millimeter-wave band in which antenna 106B may operate may be around 60 gigahertz (GHz), such as within the frequency range of 57 GHz to 64 GHz. It may be appreciated that one or more other frequencies or frequency bands may also be utilized. Semiconductor device 100B may receive power from power supply 114 coupled to processing circuit 108B via power link 204. Power supply 114 may be, among other things, a III-V compound photovoltaic cell or any other high-efficiency solar cell. Power supply 114 may generate power from a variety of light sources external to the contact lens (not depicted), such as the Sun or an indoor lighting fixture. Power supply 114 may, for example, be capable of generating approximately 10-20 microwatts (μW) of power from the indoor lighting fixture. A capacitor boost circuit embedded within processing circuit 108B may increase this power to, for example, approximately 50-100 μW for the purpose of the transmitting of the property data collected by sensor 104B by antenna 106B. It may be appreciated that the combination of sensor 104B, antenna 106B, processing circuit 108B, and power supply 114 on a single unpackaged semiconductor die may allow for a dimension of, for example, approximately 1.0 millimeter by 1.0 millimeter by avoiding the use solder connections 110 (FIG. 1A) that provide electrical connections between multiple components on a substrate 112 (FIG. 1A).

Figure 3:
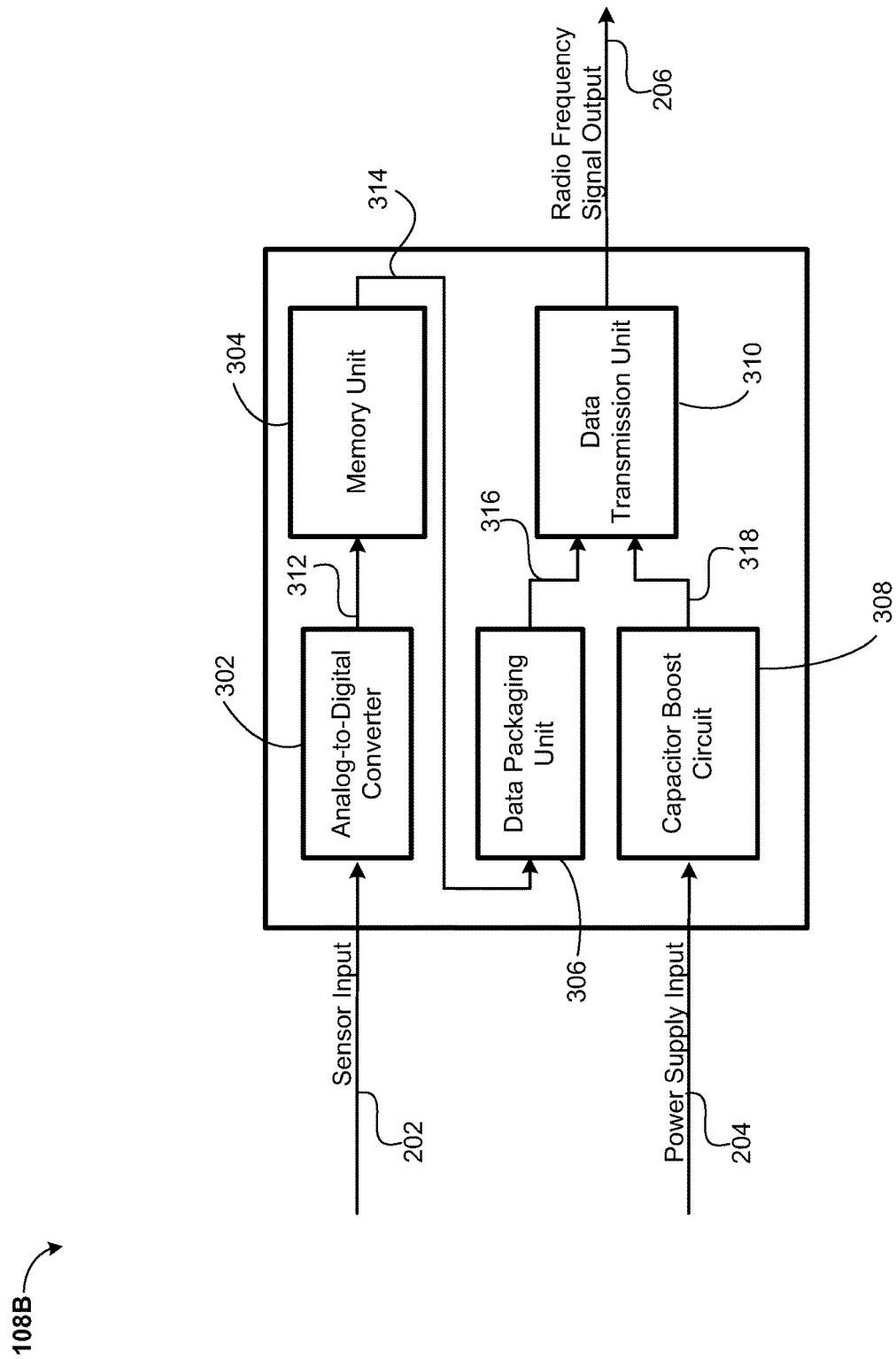
FIG. 3 is a block diagram of a processing circuit utilized within a semiconductor device to be embedded within a contact lens according to one exemplary embodiment.

FIG. 3 is an exemplary block diagram of the processing circuit 108B utilized within semiconductor device 100B of FIGS. 2A-2B. As depicted, processing circuit 108B may include, among other things, an analog-to-digital (A/D) converter 302; a memory unit 304; a data packaging unit 306; a capacitor boost circuit 308; a data transmission unit 310; data links 312, 314, and 316; and power link 318. It may be appreciated that capacitor boost circuit 308 may be incorporated external to processing circuit 108B. In operation, A/D converter 302 may receive data from sensor 104B (FIG. 1B) via data link 202 and convert the analog sensor data into a digital format. The converted digital data may be sent to memory unit 304 via data link 312. Memory unit 304 may contain, among other things, one or more look-up tables (LUTs) that may contain one or more data values corresponding to one or more properties detected by sensor 104B. Memory unit 304 may accordingly use the converted digital data received over link 312 to determine an appropriate data value for the sensor data. Memory unit 304 may then transmit the determined data value to data packaging unit 306 via data link 314. Data packaging unit 306 may, among other things, packetize the determined data value received from memory unit 304. Data packaging unit 306 may, for example, add the appropriate headers, parity bits, etc. to the determined data value to package it for transmission. The packaged data may then be transmitted to data transmission unit 310 via data link 316. Capacitor boost circuit 308 may receive power from power supply 114 (FIG. 1B) via data link 204. As discussed above, power supply 114 may, for example, be capable of generating approximately 10-20 microwatts (μW) of continuous power from a light source external to the contact lens. Capacitor boost circuit 308 may accordingly increase this power to, for example, approximately 50-100 μW by using the continuous power to charge one or more capacitors. Upon charging of the one or more capacitors, capacitor boost circuit 308 may release power in periodic bursts, so that the 10-20 μW may therefore be increased to the 50-100 μW necessary for the transmission of data via antenna 106B (FIG. 1B). Capacitor boost circuit 308 may deliver this power over power link 318 to data transmission unit 310. Data transmission unit 310 may, among other things, use the power received from power link 318 to transmit the packaged data received over data link 316 to the antenna 106B via data link 206 as an RF signal. Thus, the data corresponding to the one or more properties of the one or more analytes within the tears of the contact lens wearer may be collected by and transmitted external to the contact lens.

Figure 4A:
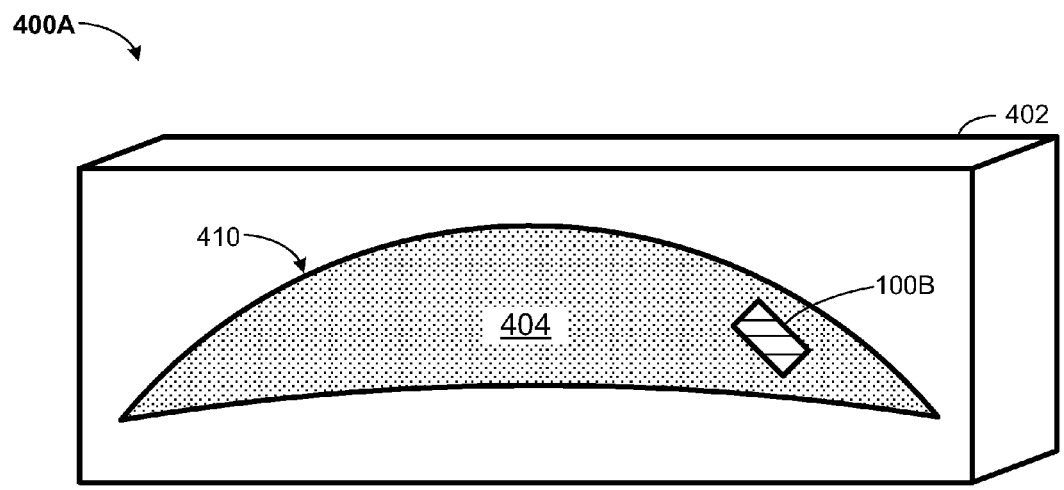
FIGS. 4A-4B are exemplary respective casting and milling methods for the manufacture of a contact lens containing an embedded semiconductor device.

Referring to FIG. 4A, a manufacturing process 400A for the manufacture of a contact lens containing an embedded semiconductor device by a casting method (e.g., spin-casting, injection molding, etc.) is depicted. Manufacturing process 400A may include a mold 402 containing a void 404. Semiconductor device 100B (FIGS. 2A-2B) may be placed within void 404 of mold 402. Void 404 may then be filled by injecting a polymeric compound (e.g., silicone hydrogel, etc.) in a liquid form. Upon solidification of the polymer, a contact lens 410 with embedded semiconductor device 100B may be formed.

Figure 4B:
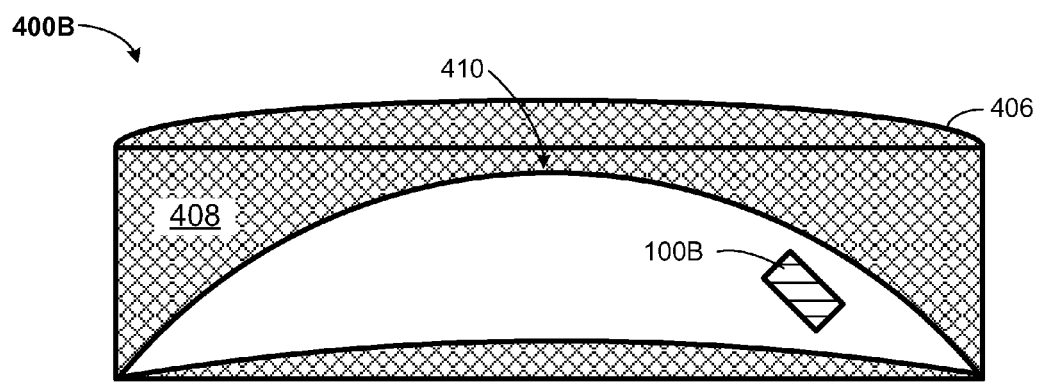

Referring to FIG. 4B, an alternative manufacturing process 400B for the manufacture of a contact lens containing an embedded semiconductor device by a milling method (e.g., single-point diamond turning) is depicted. Manufacturing process 400B may include a cylindrical disk 406 of a hard, solid polymeric compound (e.g., dried silicone hydrogel, etc.) containing an embedded semiconductor device 100B. Cylindrical disk 406 may be turned on a lathe in order to remove region 408, resulting in the formation of a contact lens 410 with embedded semiconductor device 100B. It may be appreciated that other contact lens manufacturing processes can also be utilized and/or modified for embedding semiconductor device 100B within contact lens 410.

Figure 5A:
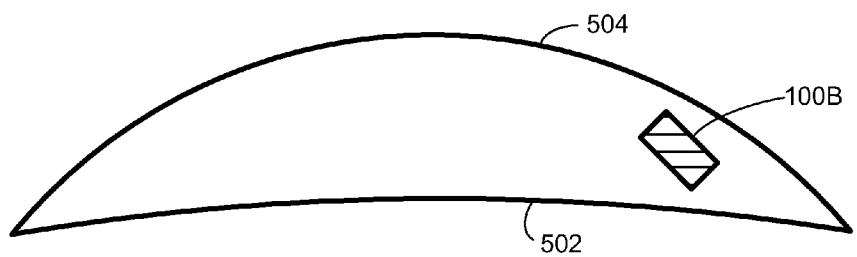
FIGS. 5A-5B are respective cross-section and plan views of a contact lens containing an embedded semiconductor device, according to one exemplary embodiment.
Figure 5B:
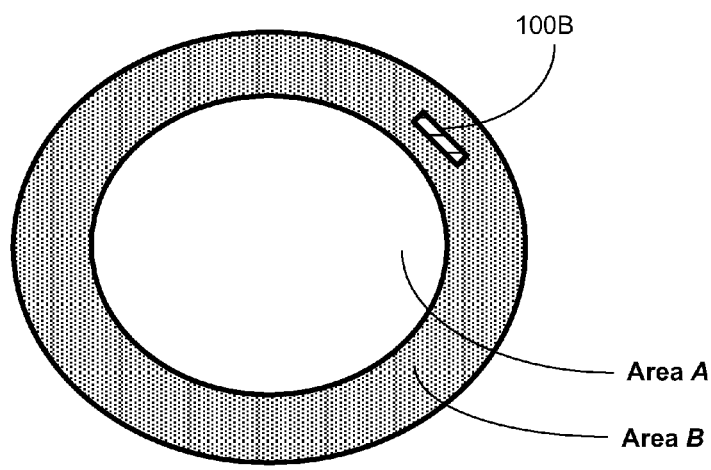

FIGS. 5A and 5B depict respective cross-section and plan views of a contact lens 410 with an embedded semiconductor device 100B, according to an exemplary embodiment. Contact lens 410 may contain, among other things, an inner surface 502 and an outer surface 504, relative to an eye of a wearer of contact lens 410. Contact lens 410 may also contain an Area A and an Area B, whereby Area A may make up at least a portion of contact lens 410 which may fall within a visual field of the eye of the wearer and consequently be used for vision. Conversely, Area B may make up at least another portion of contact lens 410 which may fall outside of the visual field of the eye of the wearer and consequently not be used for vision. Accordingly, semiconductor device 100B may be embedded within a least a portion of Area B, such that semiconductor device 100B falls outside of the visual field of the wearer of contact lens 410 and may, therefore, not obstruct the visual field of the wearer of contact lens 410.

Figure 6:
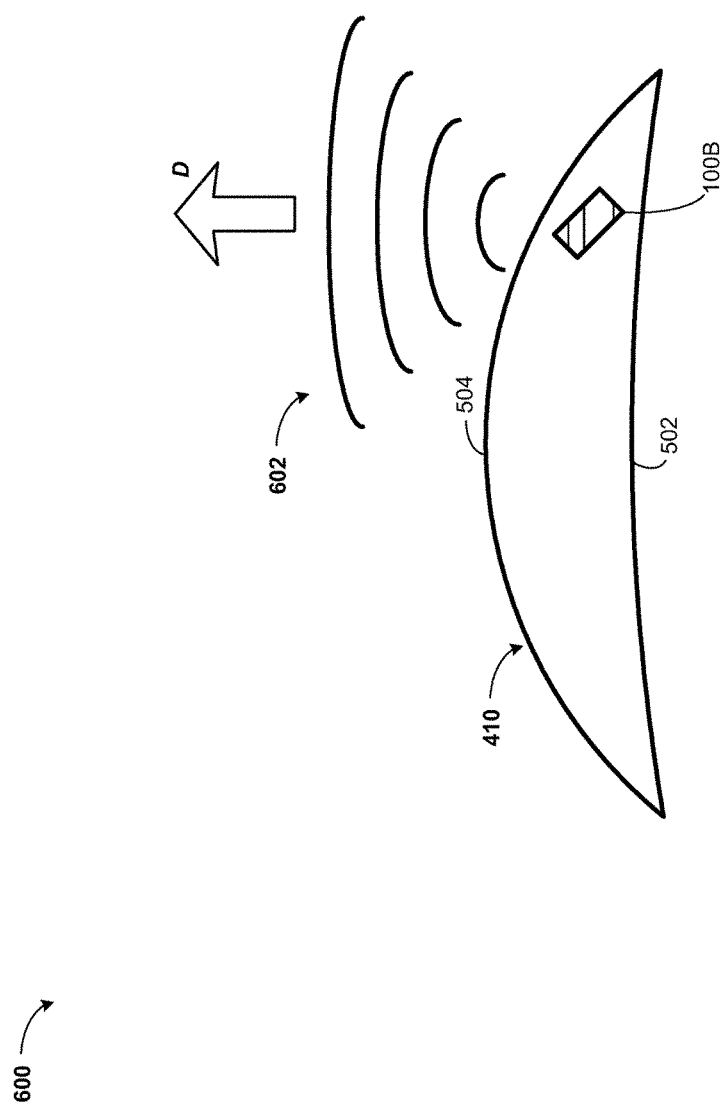
FIG. 6 is an operational diagram of a semiconductor device embedded within a contact lens, according to one exemplary embodiment.

Referring to FIG. 6, an operational diagram 600 of a contact lens 410 containing an embedded semiconductor device 100B is depicted. Semiconductor 100B may, among other things, generate an RF signal 602 containing data corresponding to the sensing of one or more properties associated with one or more analytes in the tears of the wearer of contact lens 410. The generated RF signal 602 may be transmitted in a direction D away from outer surface 504, which may avoid or mitigate the transmission of RF power towards the inner surface 502 of the contact lens 410. Thus, generated RF may be transmitted in an outward direction from the wearer of contact lens 410. Accordingly, the wearer of contact lens 410 may not be subjected to in-bound RF radiation, minimizing impairment to the contact lens wearer's health (e.g., burns to the eye, brain tumor).

Figure 7:
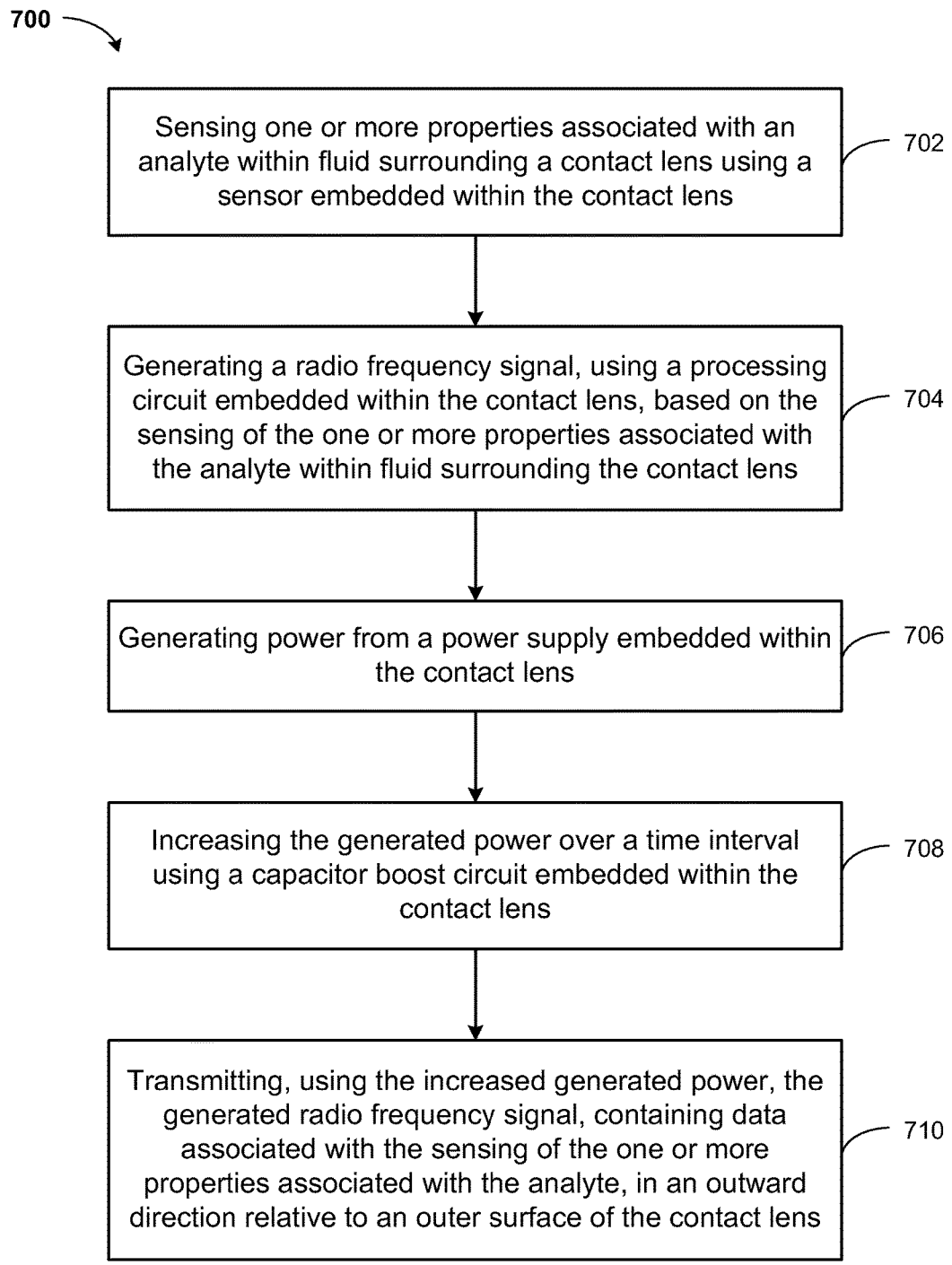
FIG. 7 is an operational flow chart corresponding to a process for determining one or more properties associated with an analyte within fluid surrounding a contact lens according to one exemplary embodiment.

FIG. 7 is an operational flow chart 700 corresponding to a process for determining one or more properties associated with an analyte within fluid surrounding a contact lens according to the exemplary embodiment depicted in FIG. 2B and FIG. 3. The operational flow chart 700 of FIG. 7 may be described with the aid of the exemplary embodiments of FIG. 2B and FIG. 3.

At 702, one or more properties associated with an analyte (e.g., glucose, medication, etc.) within fluid surrounding a contact lens (e.g., concentration) using a sensor embedded within the contact lens is sensed. In operation, sensor 104B (FIGS. 2A-2B) of semiconductor device 100B (FIGS. 2A-2B) may detect a pre-determined property of one or more analytes present within the tears of a wearer of a contact lens. These properties may accordingly include, among other things, detection of the presence or absence of the one or more analytes or a concentration value associated with the one or more analytes. The one or more analytes may include, among other things, glucose, medications, and ionic compounds (e.g. salts of sodium, calcium, potassium, etc.). Sensor 104B may generate a data signal based on the sensing of the one or more properties and transmit the signal to processing circuit 108B (FIG. 2B) via data link 202 (FIG. 2B).

At 704, a radio frequency (RF) signal is generated, using a processing circuit embedded within the contact lens, based on the sensing of the one or more properties associated with the analyte within fluid surrounding the contact lens. In operation, processing circuit 108B (FIG. 2B) may receive the data signal generated by sensor 104B (FIG. 2B) via data link 202 (FIG. 2B) and convert the received data signal into an RF signal that may be transmitted by antenna 106B (FIG. 2B).

At 706, power is generated from a power supply embedded within the contact lens. In operation, power supply 114 (FIG. 2B) may be, among other things, a III-V compound photovoltaic cell that may generate, for example, 10-20 μW of continuous power from a variety of light sources external to the contact lens (e.g., the Sun, an indoor lamp, etc.). Power supply 114 may transmit the generated power to processing circuit 108B (FIG. 2B) via power link 204 (FIG. 2B) in order to provide power to processing circuit 108B.

At 708, the generated power is increasing over a time interval using a capacitor boost circuit embedded within the contact lens. In operation, capacitor boost circuit 308 (FIG. 3) may receive power from power supply 114 (FIG. 2B) via power link 204 (FIG. 3). Capacitor boost circuit 308 may increase the power received via power link 204 to, for example, approximately 50-100 μW by charging one or more capacitors and discharging the one or more charged capacitors in periodic bursts, so that the 10-20 μW may therefore be increased to the 50-100 μW necessary for the transmission of data via antenna 106B (FIG. 2B).

At 710, the generated RF signal is transmitted, using the increased generated power, whereby the RF signal contains data associated with the sensing of the one or more properties associated with the analyte, in an outward direction D (FIG. 6) relative to an outer surface 504 (FIG. 6) of the contact lens 410 (FIG. 6). In operation, processing circuit 108B (FIG. 2B) may be coupled to antenna 106B (FIG. 2B) via data link 206 (FIG. 2B). Processing circuit 108B may transmit the generated RF signal to a reader device external to the contact lens (not depicted). Accordingly, the transmitted RF signal may contain, among things, data corresponding to the one or more properties of the one or more analytes as detected by sensor 104B (FIG. 2B).

Figure 8:
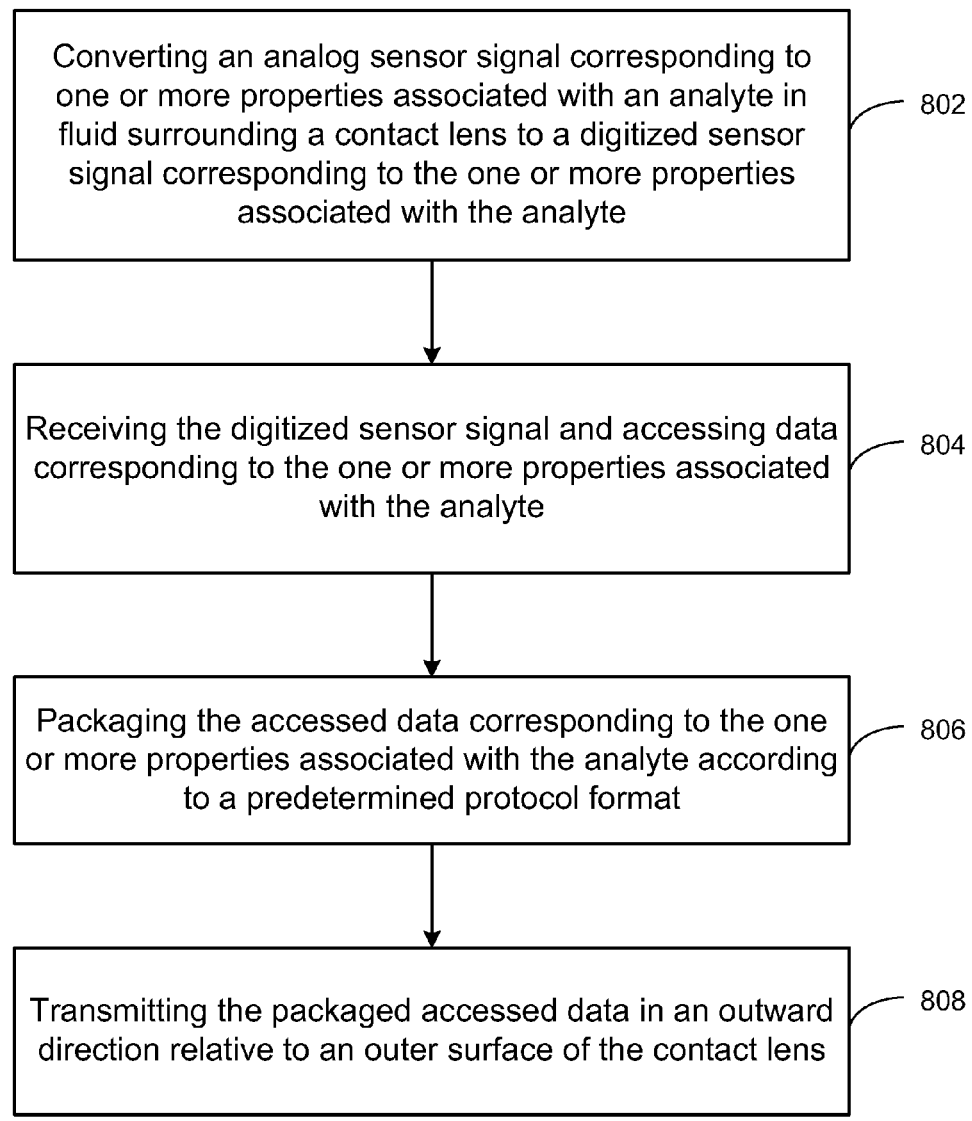
FIG. 8 is an operation flow chart corresponding to a process for generating a radio frequency signal to be transmitted by a semiconductor device embedded within a contact lens, according to one exemplary embodiment.

FIG. 8 depicts an exemplary operational flow chart describing the radio frequency (RF) signal generation process 704 within the operational flow chart 700 of FIG. 7. FIG. 8 is described with the aid of the exemplary embodiments of FIG. 2B and FIG. 3.

At 802, an analog sensor signal corresponding to one or more properties associated with an analyte in fluid surrounding a contact lens is converted to a digitized sensor signal corresponding to the one or more properties associated with the analyte. In operation, analog-to-digital (A/D) converter 302 (FIG. 3) may receive an analog input from sensor 104B (FIG. 2B) via data link 202 (FIG. 3). A/D converter 302 may convert the analog sensor data into a digital format. The converted digital data may be sent to memory unit 304 (FIG. 3) via data link 312 (FIG. 3).

At 804, the digitized sensor signal is received and data corresponding to the one or more properties associated with the analyte is accessed. In operation, memory unit 304 (FIG. 3) may contain one or more look-up tables (LUTs) that may contain one or more data values corresponding to one or more properties detected by sensor 104B (FIG. 2B). Memory unit 304 may accordingly use the converted digital data received over link 312 (FIG. 3) to determine an appropriate data value or information for the sensor data. Memory unit 304 may then transmit the determined data value or information to data packaging unit 306 (FIG. 3) via data link 314 (FIG. 3).

At 806, the accessed data corresponding to the one or more properties associated with the analyte is packaged according to a predetermined protocol format. In operation, data packaging unit 306 (FIG. 3) may packetize the determined data value received from memory unit 304 (FIG. 3). Data packaging unit 306 may, for example, add the appropriate headers, parity bits, etc. to the determined data value or information to package it for transmission. The packaged data may then be transmitted to data transmission unit 310 (FIG. 3) via data link 316 (FIG. 3).

At 808, the packaged accessed data is transmitted in an outward direction D (FIG. 6) relative to an outer surface 504 (FIG. 6) of the contact lens 410 (FIG. 6). In operation, data transmission unit 310 (FIG. 3) may use the power received over power link 318 (FIG. 3) from capacitor boost circuit 308 (FIG. 3) to transmit the packaged data received over data link 316 (FIG. 3) to antenna 106B (FIG. 2B) via data link 206 (FIG. 3). Thus, an RF signal corresponding to one or more properties associated with one or more analytes is generated.

The semiconductor device 100B (FIG. 6) that is embedded within contact lens 410 (FIG. 5) may operate over the millimeter-wave band (i.e., 57-64 GHz) in order to reduce the physical dimensions of antenna 106B (FIG. 2B) and benefit from high atmospheric oxygen absorption for enhancing frequency reuse. Based on enhancing frequency reuse, multiple contact lens wearers in proximity with each other can unidirectionally transmit an outbound (i.e., away from lens wearer's eye) RF signal corresponding to the one or more properties associated with the one or more analytes without encountering frequency interference. Further, the use of a high-efficiency power supply (e.g., high-efficiency solar cell) coupled with power boost circuitry, and the reduced dimensionality associated with the antenna 106B, among things, establishes semiconductor device 100B (FIG. 2B) as a self-contained semiconductor chip with no requisite need for interfacing with one or more other components (i.e., antennas, processing (Transmit/Receiver circuitry, etc.) through I/O pins such as wirebonds and/or C4 connections.

Figure 9:
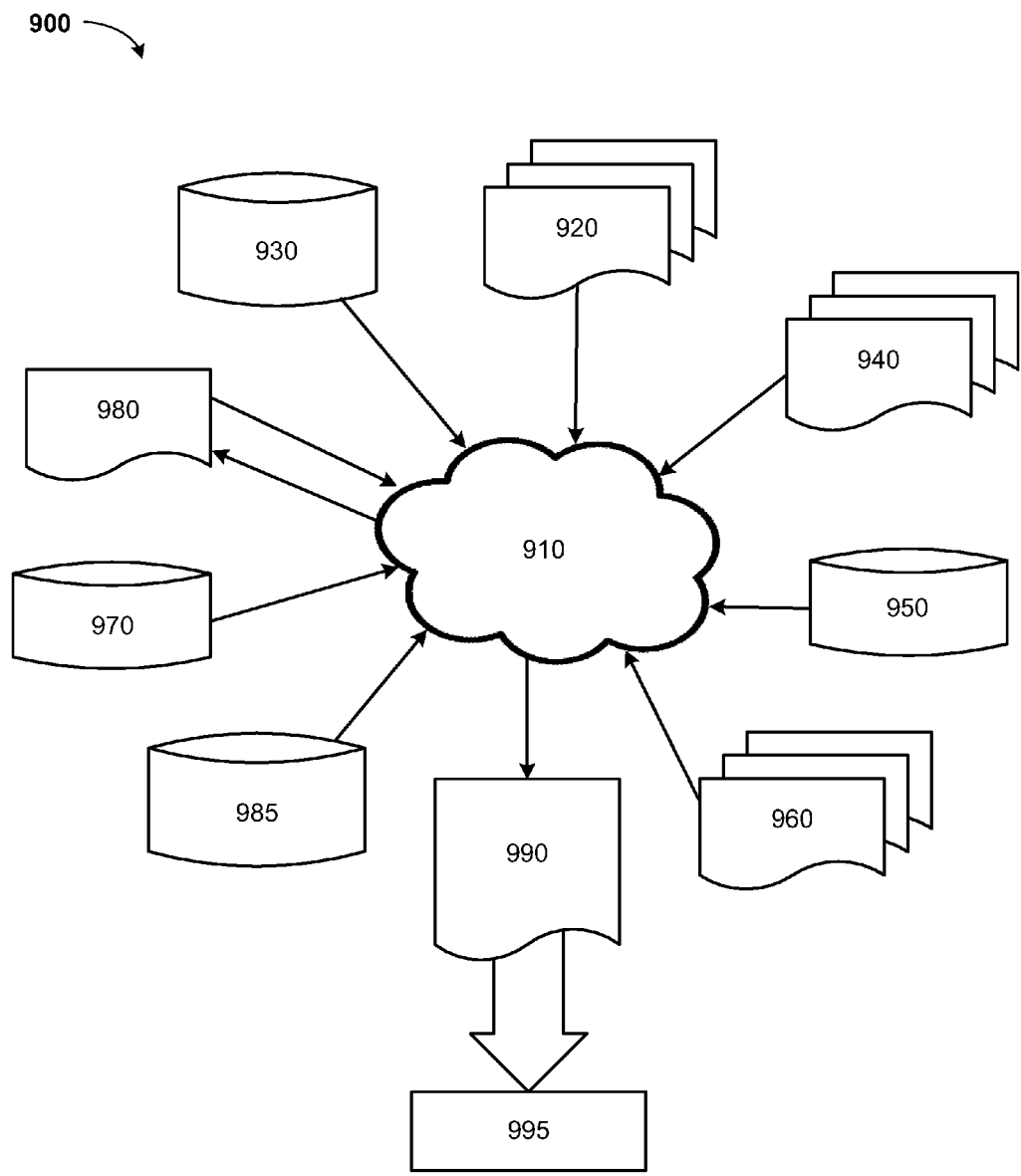
FIG. 9 is a flow diagram of a design process used in semiconductor design, manufacture, and/or test.

FIG. 9 shows a block diagram of an exemplary design flow 900 used for example, in semiconductor IC logic design, simulation, test, layout, and manufacture. Design flow 900 includes processes, machines and/or mechanisms for processing design structures or devices to generate logically or otherwise functionally equivalent representations of the design structures and/or devices described above and shown in FIGS. 2A-2B and FIG. 3. The design structures processed and/or generated by design flow 900 may be encoded on machine-readable transmission or storage media to include data and/or instructions that when executed or otherwise processed on a data processing system generate a logically, structurally, mechanically, or otherwise functionally equivalent representation of hardware components, circuits, devices, or systems. Machines include, but are not limited to, any machine used in an IC design process, such as designing, manufacturing, or simulating a circuit, component, device, or system. For example, machines may include: lithography machines, machines and/or equipment for generating masks (e.g. e-beam writers), computers or equipment for simulating design structures, any apparatus used in the manufacturing or test process, or any machines for programming functionally equivalent representations of the design structures into any medium (e.g. a machine for programming a programmable gate array).

Design flow 900 may vary depending on the type of representation being designed. For example, a design flow 900 for building an application specific IC (ASIC) may differ from a design flow 900 for designing a standard component or from a design flow 900 for instantiating the design into a programmable array, for example a programmable gate array (PGA) or a field programmable gate array (FPGA) offered by Altera® Inc. or Xilinx® Inc.

FIG. 9 illustrates multiple such design structures including an input design structure 920 that is preferably processed by a design process 910. Design structure 920 may be a logical simulation design structure generated and processed by design process 910 to produce a logically equivalent functional representation of a hardware device. Design structure 920 may also or alternatively comprise data and/or program instructions that when processed by design process 910, generate a functional representation of the physical structure of a hardware device. Whether representing functional and/or structural design features, design structure 920 may be generated using electronic computer-aided design (ECAD) such as implemented by a core developer/designer. When encoded on a machine-readable data transmission, gate array, or storage medium, design structure 920 may be accessed and processed by one or more hardware and/or software modules within design process 910 to simulate or otherwise functionally represent an electronic component, circuit, electronic or logic module, apparatus, device, or system such as those shown in FIGS. 2A-2B and FIG. 3. As such, design structure 920 may comprise files or other data structures including human and/or machine-readable source code, compiled structures, and computer-executable code structures that when processed by a design or simulation data processing system, functionally simulate or otherwise represent circuits or other levels of hardware logic design. Such data structures may include hardware-description language (HDL) design entities or other data structures conforming to and/or compatible with lower-level HDL design languages such as Verilog and VHDL, and/or higher level design languages such as C or C++.

Design process 910 preferably employs and incorporates hardware and/or software modules for synthesizing, translating, or otherwise processing a design/simulation functional equivalent of the components, circuits, devices, or logic structures shown in FIGS. 2A-2B and FIG. 3 to generate a Netlist 980 which may contain design structures such as design structure 920. Netlist 980 may comprise, for example, compiled or otherwise processed data structures representing a list of wires, discrete components, logic gates, control circuits, I/O devices, models, etc. that describes the connections to other elements and circuits in an integrated circuit design. Netlist 980 may be synthesized using an iterative process in which netlist 980 is resynthesized one or more times depending on design specifications and parameters for the device. As with other design structure types described herein, netlist 980 may be recorded on a machine-readable data storage medium or programmed into a programmable gate array. The medium may be a non-volatile storage medium such as a magnetic or optical disk drive, a programmable gate array, a compact flash, or other flash memory. Additionally, or in the alternative, the medium may be a system or cache memory, buffer space, or electrically or optically conductive devices and materials on which data packets may be transmitted and intermediately stored via the Internet, or other networking suitable means.

Design process 910 may include hardware and software modules for processing a variety of input data structure types including Netlist 980. Such data structure types may reside, for example, within library elements 930 and include a set of commonly used elements, circuits, and devices, including models, layouts, and symbolic representations, for a given manufacturing technology (e.g., different technology nodes, 32 nm, 45 nm, 90 nm, etc.). The data structure types may further include design specifications 940, characterization data 950, verification data 960, design rules 970, and test data files 985 which may include input test patterns, output test results, and other testing information. Design process 910 may further include, for example, standard mechanical design processes such as stress analysis, thermal analysis, mechanical event simulation, process simulation for operations such as casting, molding, and die press forming, etc. One of ordinary skill in the art of mechanical design can appreciate the extent of possible mechanical design tools and applications used in design process 910 without deviating from the scope and spirit of the invention. Design process 910 may also include modules for performing standard circuit design processes such as timing analysis, verification, design rule checking, place and route operations, etc.

Design process 910 employs and incorporates logic and physical design tools such as HDL compilers and simulation model build tools to process design structure 920 together with some or all of the depicted supporting data structures along with any additional mechanical design or data (if applicable), to generate a second design structure 990. Design structure 990 resides on a storage medium or programmable gate array in a data format used for the exchange of data of mechanical devices and structures (e.g. information stored in a IGES, DXF, Parasolid XT, JT, DRG, or any other suitable format for storing or rendering such mechanical design structures). Similar to design structure 920, design structure 990 preferably comprises one or more files, data structures, or other computer-encoded data or instructions that reside on transmission or data storage media and that when processed by an ECAD system generate a logically or otherwise functionally equivalent form of one or more of the embodiments of the invention shown in FIGS. 2A-2B and FIG. 3. In one embodiment, design structure 990 may comprise a compiled, executable HDL simulation model that functionally simulates the devices shown in FIGS. 2A-2B and FIG. 3.

Design structure 990 may also employ a data format used for the exchange of layout data of integrated circuits and/or symbolic data format (e.g. information stored in a GDSII (GDS2), GL1, OASIS, map files, or any other suitable format for storing such design data structures). Design structure 990 may comprise information such as, for example, symbolic data, map files, test data files, design content files, manufacturing data, layout parameters, wires, levels of metal, vias, shapes, data for routing through the manufacturing line, and any other data required by a manufacturer or other designer/developer to produce a device or structure as described above and shown in FIGS. 2A-2B and FIG. 3. Design structure 990 may then proceed to a stage 995 where, for example, design structure 990: proceeds to tape-out, is released to manufacturing, is released to a mask house, is sent to another design house, is sent back to the customer, etc.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the one or more embodiment, the practical application or technical improvement over technologies found in the marketplace, or to enable others of ordinary skill in the art to understand the embodiments disclosed herein.

What is claimed is:

1. A semiconductor device embedded within a contact lens, the semiconductor device comprising:
    a sensor that determines one or more properties associated with an analyte within fluid surrounding the contact lens;
    a processing circuit coupled to the sensor, wherein the processing circuit generates a signal associated with the one or more determined properties associated with the analyte;
    a power supply coupled to the processing circuit for providing DC power to the processing circuit;
    a boost circuit coupled to the power supply, the boost circuit increasing the provided DC power of the power supply for transmitting the signal generated by the processing circuit; and
    a directional antenna coupled to the processing circuit for transmitting the generated signal in an outward direction relative to an outer surface of the contact lens, wherein the transmission of the signal in the outward direction minimizes health impairment to a wearer of the contact lens,
    wherein the sensor, the processing circuit, the power supply, the boost circuit, and the directional antenna are contained on a single self-contained unpackaged semiconductor die having no input-output pins, wire bonds, nor controlled collapse chip connections to one or more other components.

2. The semiconductor device of claim 1, wherein the boost signal comprises a capacitor boost circuit.

3. The semiconductor device of claim 1, wherein the power supply comprises a III-V compound photovoltaic cell.

4. The semiconductor device of claim 1, wherein the one or more determined properties associated with the analyte comprises a concentration value corresponding to one or more of glucose, medications, calcium, potassium, and sodium.

5. The semiconductor device of claim 1, wherein the directional antenna comprises an on-chip Yagi antenna operating at a millimeter-wave band.

6. The semiconductor device of claim 5, wherein the on-chip Yagi antenna operates within a 60 Gigahertz (GHz) region of an electromagnetic spectrum.

7. The semiconductor device of claim 1, wherein the single unpackaged semiconductor die includes a dimension of about 1.0 millimeter by 1.0 millimeter.

8. The semiconductor device of claim 1, wherein the processing circuit comprises:
   an analog to digital (A/D) convertor coupled to the sensor, wherein the A/D convertor converts an analog sensor signal corresponding to the one or more properties associated with the analyte to a digitized sensor signal corresponding to the one or more properties associated with the analyte.

9. The semiconductor device of claim 8, wherein the processing circuit comprises:
   a memory unit coupled to the A/D convertor, wherein the memory unit includes a look-up table that receives the digitized sensor signal and accesses data corresponding to the one or more properties associated with the analyte.

10. The semiconductor device of claim 9, wherein the processing circuit comprises:
    a data packaging unit coupled to the memory unit, wherein the data packaging unit packages the accessed data corresponding to the one or more properties associated with the analyte according to a predetermined protocol format.

11. The semiconductor device of claim 10, wherein the processing circuit comprises:
    a radio frequency transmitter coupled to the data packaging unit, wherein the radio frequency transmitter transmits the packaged accessed data in an outward direction relative to an outer surface of the contact lens.

12. A method of processing one or more properties associated with an analyte within fluid surrounding a contact lens, the method comprising:
    sensing the one or more properties associated with the analyte within fluid surrounding the contact lens using a sensor embedded within the contact lens;
    generating a radio frequency signal using a processing circuit based on the sensing of the one or more properties associated with the analyte within fluid surrounding the contact lens, wherein the processing circuit is embedded within the contact lens;
    generating power from a power supply embedded within the contact lens;
    increasing the generated power over a time interval using a capacitor boost circuit, wherein the capacitor boost circuit is embedded within the contact lens; and
    transmitting, using the increased generated power, the generated radio frequency signal in an outward direction relative to an outer surface of the contact lens using a directional antenna, wherein the generated radio frequency signal includes data associated with the sensing of the one or more properties associated with the analyte,
    wherein the embedded sensor, the embedded processing circuit, the embedded power supply, and the embedded capacitor boost circuit are contained on a single unpackaged semiconductor die embedded within the contact lens.

13. The method of claim 12, wherein the one or more determined properties associated with the analyte comprises a concentration value corresponding to one or more of glucose, medications, calcium, potassium, and sodium.

14. The method of claim 12, wherein the generating of the radio frequency signal using the processing circuit comprises:
    converting an analog sensor signal corresponding to the one or more properties associated with the analyte to a digitized sensor signal corresponding to the one or more properties associated with the analyte;
    receiving the digitized sensor signal and accessing data corresponding to the one or more properties associated with the analyte;
    packaging the accessed data corresponding to the one or more properties associated with the analyte according to a predetermined protocol format; and
    transmitting the packaged accessed data in an outward direction relative to an outer surface of the contact lens.

15. The method of claim 12, wherein the directional antenna comprises an on-chip Yagi antenna operating at a millimeter-wave band.

16. The method of claim 15, wherein the on-chip Yagi antenna operates at about 60 Gigahertz (GHz).

17. The method of claim 12, wherein the single unpackaged semiconductor die includes a dimension of about 1.0 millimeter by 1.0 millimeter.

18. The method of claim 12, wherein the single unpackaged semiconductor die consists of a self-contained semiconductor chip with no input-output pins, wire bonds, or controlled collapse chip connections to one or more other components.

19. The method of claim 12, wherein the transmission of the signal in the outward direction minimizes health impairment to a wearer of the contact lens.

* * * * *